United States Patent [19]

Mues et al.

[11] 4,328,219
[45] May 4, 1982

[54] 2-SUBSTITUTED BENZAZOLE PESTICIDE SYNERGISTS

[75] Inventors: Volker Mues, Wuppertal; Wolfgang Behrenz, Overath, both of Fed. Rep. of Germany

[73] Assignee: Bayer Aktiengesellschaft, Leverkusen, Fed. Rep. of Germany

[21] Appl. No.: 129,853

[22] Filed: Mar. 12, 1980

[30] Foreign Application Priority Data

Apr. 14, 1979 [DE] Fed. Rep. of Germany ....... 2913527

[51] Int. Cl.³ .................... A01N 43/76; A01N 43/78; C07D 263/58; C07D 277/68
[52] U.S. Cl. .................................. 424/200; 424/187; 424/211; 424/216; 424/217; 424/270; 424/272; 548/152; 548/217; 548/221
[58] Field of Search ............... 548/217; 424/272, 270, 424/187, 200, 211, 216, 217

[56] References Cited

U.S. PATENT DOCUMENTS 3,452,036  6/1969  Crocker et al. .................... 548/217
3,840,550 10/1974  Brenneisen et al. ............... 424/270
3,876,791  4/1975  Hubbard et al. ................... 424/270

FOREIGN PATENT DOCUMENTS 2355092  5/1975  Fed. Rep. of Germany ...... 548/217

OTHER PUBLICATIONS

Elwood et al., "J. Org. Chem.", vol. 32, (1967), pp. 2956-2959.

Primary Examiner—Anton H. Sutto

Attorney, Agent, or Firm—Sprung, Horn, Kramer & Woods

[57] ABSTRACT

2-Substituted benzazoles of the formula

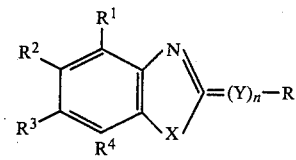

in which
R represents optionally substituted alkyl, alkenyl, alkynyl, cycloalkyl, optionally substituted aryl or optionally substituted aralkyl,
$R^1$, $R^2$, $R^3$ and $R^4$ independently of one another represent hydrogen, halogen, optionally halogen-substituted alkyl, optionally halogen-substituted alkoxy, nitro, cyano, alkylcarbonyl or alkoxycarbonyl, or two radicals in combination form a benzo radical,
X and Y independently of one another represent oxygen or sulphur and
n represents zero or 1, synergize conventional pesticides. Those benzazoles in which
R is —$CH_2$—C≡≡CH,
$R^1$, $R^2$, $R^3$ and $R^4$ represent independently of one another hydrogen or halogen (preferably chlorine),
Y represents oxygen and
n represents 1, are new and exhibit particularly high synergistic activity.

7 Claims, No Drawings

2-SUBSTITUTED BENZAZOLE PESTICIDE SYNERGISTS

The invention relates to new pesticidal (in particular insecticidal and acaricidal) synergistic combinations of certain substituted benzazoles, some of which are known, and certain other known pesticidal active compounds.

It is already known that the following active compounds and groups of active compounds have pesticidal properties, in particular insecticidal and acaricidal properties:

(A) carbamates, for example 2-iso-propoxy-phenyl N-methyl-carbamate, 3,4,5-trimethyl-phenyl N-methyl-carbamate, 1-naphthyl N-methyl-carbamate, 2,3-dihydro-2,2-dimethyl-7-benzofuranyl N-methyl-carbamate, 2-(1,3-dioxolan-2-ylphenyl) N-methyl-carbamate and 2,2-dimethyl-1,3-benzodioxol-4-yl N-methyl-carbamate;

(B) carboxylic acid esters, for example 2,3,4,5-tetrahydro-phthalimido-methyl chrysanthemate and (5-benzyl-3-furyl)-methyl 2,2-dimethyl-3-(2-methylpropenyl)-cyclopropanecarboxylate;

(C) phosphoric acid esters, for example O,O-dimethyl O-(2,2-dichlorovinyl) phosphoric acid ester; and (D) halogenoalkanes, for example 1,1,1-trichloro-2,2-bis(4-methoxyphenyl)-ethane and 1,1,1-trichloro-2,2-bis-(4-chlorophenyl)-ethane.

Synergistic mixtures of carbamates, for example 2-iso-propoxy-phenyl N-methylcarbamate, or of phosphoric acid esters, for example O,O-diethyl O-(2-isopropyl-4-methylpyrimidin-6-yl) thionophosphoric acid ester, or of naturally occurring or synthetic pyrethroids and piperonyl ethers, for example α-(2-(2-butoxy-ethoxy)-ethoxy)-4,5-methylenedioxy-2-propyl-toluene, are also known (see Bull. Org. mond. Santé/Bull. Wld. Hlth Org. 1966, 35, 691–708; and Schrader, G., Die Entwicklung neuer insektizider Phosphor-säureester (The Development of New Insecticidal Phosphoric Acid Esters) 1963, page 158). However, the activity of these synergistic active compound combinations is unsatisfactory. Only α-(2-(2-butoxy-ethoxy)-ethoxy)-4,5-methylenedioxy-2-propyl-toluene has hitherto achieved a certain importance in practice.

The present invention now provides a pesticidal composition containing as active ingredients (1) at least one substituted benzazole of the general formula

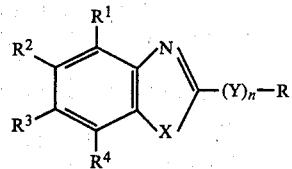

in which
R represents optionally substituted alkyl, alkenyl, alkynyl, cycloalkyl, optionally substituted aryl or optionally substituted aralkyl,
$R^1$, $R^2$, $R^3$ and $R^4$ independently of one another represent hydrogen, halogen, optionally halogensubstituted alkyl, optionally halogen-substituted alkoxy, nitro, cyano, alkylcarbonyl or alkoxycarbonyl, or two radicals in combination form a benzo radical.

X and Y independently of one another represent oxygen or sulphur and
n represents zero or 1,
and (2) at least one pesticidally active compound, in particular an arthropodicidally active compound, especially an insecticidally or acaricidally active compound. The present compositions have a particularly high pesticidal action, in particular an exceptionally high insecticidal and acaricidal action.

Active compound combinations of substituted benzazoles of the formula (I) and pesticidal compounds selected from (A) carbamates, (B) carboxylic acid esters, including the naturally occurring and synthetic pyrethroids, (C) phosphoric acid esters and phosphonic acid esters and (D) halogenoalkanes are preferred.

The synergistic action of the compounds of the general formula (I) manifests itself particularly markedly with the preferred active compounds described below.

Preferred carbamates (A) are those of the general formula

in which
$R^1$ represents aryl, a heterocyclic radical or an oxime radical, each being optionally substituted,
$R^2$ represents hydrogen or an alkyl radical with 1 to 4 carbon atoms and
$R^3$ represents alkyl, alkylcarbonyl with 1 to 6 carbon atoms in the alkyl radical, which can optionally also be substituted by hydroxyl or methylthio, or the radical —S—Z,
wherein Z represents an aliphatic radical which has 1 to 4 carbon atoms and is optionally substituted by halogen (especially $CCl_3$ or $CF_3$) or an aryl radical (especially phenyl) which is optionally substituted, preferably by nitrile, halogen, (especially chlorine), methyl, trihalogenomethyl, trifluoromethylmercapto or nitro, or represents methoxycarbonyl or the radical

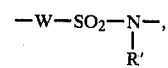

wherein
R' represents hydrogen or methyl and
W represents alkyl, halogenoalkyl, alkylamino, dialkylamino or an aryl radical which is optionally substituted, preferably by halogen, trihalogenomethyl, nitrile, methyl or nitro.

Carbamates of the formula (II) wherein
$R^1$ represents phenyl or naphthyl, optionally substituted by alkyl, alkenyl, alkoxy, alkylthio or alkylthioalkyl with in each case 1 to 6 carbon atoms, dialkylamino or dialkenylamino with up to 3 carbon atoms per alkyl or alkenyl part, halogen (especially chlorine), dioxolanyl or the radical

are particularly preferred.

Carbamates of the formula (II) wherein $R^1$ represents 2,3-dihydrobenzofuranyl, benzodioxolyl, benzothienyl, pyrimidinyl or pyrazolyl, in each case optionally substituted by alkyl with 1 to 4 carbon atoms, (especially methyl) or by dialkylamino with 1 to 4 carbon atoms per alkyl part, are also particularly preferred.

Carbamates of the general formula (II) wherein R¹ represents a radical of the general formula

in which

R⁴ and R⁵ are identical or different and represent alkyl, cycloalkyl, alkenyl, alkynyl, alkoxy, alkylthio, alkoxycarbonyl, alkylcarbamoyl or alkylthioalkyl, with in each case up to 6 carbon atoms, cyano or phenyl, or R⁴ and R⁵ together with the adjacent C-atom represent a dioxolanyl or dithiolanyl radical which is optionally substituted by $C_{1-4}$-alkyl, are also particularly preferred.

The following carbamates of the formula (II) may be mentioned in particular: 2-methylphenyl, 2-ethylphenyl, 2-n-propylphenyl, 2-methoxyphenyl, 2-ethoxyphenyl, 2-isopropoxyphenyl, 4-methylphenyl, 4-ethylphenyl, 4-n-propylphenyl, 4-methoxyphenyl, 4-ethoxyphenyl, 4-n-propoxyphenyl, 3,4,5-trimethylphenyl, 1-naphthyl, 2,3-dihydro-2,2-dimethyl-7-benzofuranyl, 2-(1,3-dioxolan-2-yl-phenyl) and 2,2-dimethyl-1,3-benzodioxol-4-yl N-methyl-carbamate and the corresponding N-methyl-N-acetyl-, N-methyl-N-trifluoromethylthio-, N-methyl-N-dichloromonofluoromethylthio- and N-methyl-N-dimethylaminothio-carbamates.

Preferred carboxylic acid esters (B) are those of the general formula

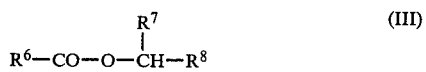

in which

R⁶ represents an alkyl, aralkyl, aryl or cycloalkyl radical, which can optionally be substituted, R⁷ represents hydrogen, alkyl, halogenoalkyl, alkenyl, alkynyl or cyano and R⁸ represents aryl or a heterocyclic radical or R⁷ and R⁸, together with the methine group to which they are bonded, form an optionally substituted cyclopentenone ring.

Carboxylic acid esters of the formula (III) in which R⁶ represents alkyl which has 1 to 6 carbon atoms and is optionally substituted by optionally halogen-substituted phenyl, or represents cyclopropyl which is optionally substituted by alkyl, alkenyl, halogenoalkyl or halogenoalkenyl, with in each case up to 6 carbon atoms, or represents phenyl which is optionally substituted by halogen, and in which R⁷ represents hydrogen, alkyl with 1 to 6 carbon atoms, halogenoalkyl with 1 to 4 carbon atoms and up to 3 halogen atoms, cyano or ethynyl, are particularly preferred.

Carboxylic acid esters of the formula (III) in which

R⁸ represents phenyl which is optionally substituted by $C_{1-4}$-alkyl, halogen (especially fluorine or chlorine), optionally halogen- or methyl-substituted phenoxy or optionally substituted benzyl, or represents furanyl, tetrahydrophthalimido or benzodioxole, in each case optionally substituted by halogen (especially chlorine), alkyl with up to 4 carbon atoms, alkenyl with up to 4 carbon atoms or benzyl or R⁷ and R⁸, together with the methine group to which they are bonded, form a cyclopentenone group which is optionally substituted by $C_{1-4}$-alkyl, furfuryl or $C_{1-5}$-alkenyl, are also particularly preferred.

Specific compounds (B) which may be mentioned are: acetic acid 1-(3,4-dichlorophenyl)-2,2,2-trichloroethyl ester, 2,3,4,5-tetrahydrophthalimidomethyl chrysanthemate and (5-benzyl-3-furyl)-methyl 2,2-dimethyl-3-(2-methylpropenyl)-cyclopropanecarboxylate. The naturally occurring pyrethroids are also particularly preferred.

Preferred phosphoric acid esters and phosphonic acid esters (C) are those of the general formula

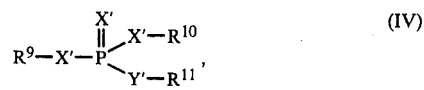

in which the radicals X' independently of one another represent O or S,

Y' represents O, S, —NH— or a direct bond between the central P atom and R¹¹,

R⁹ and R¹⁰ are identical or different and represent an optionally substituted alkyl or aryl group and R¹¹ represents an optionally substituted alkyl, aryl, heteroaryl, aralkyl, alkenyl or dioxanyl group, an oxime radical or a radical identical to that to which it is bonded. Phosphoric acid esters and phosphonic acid esters of the formula (IV) in which R⁹ and R¹⁰ are identical or different and represent $C_{1-4}$-alkyl or phenyl, and R¹¹ represents alkyl which has 1 to 4 carbon atoms and is optionally substituted by halogen, hydroxyl, cyano, optionally halogen-substituted phenyl, carbamoyl, alkylsulphonyl, alkylsulphinyl, alkylcarbonyl, alkoxy, alkylmercapto or alkoxycarbonyl, the last six groups having in each case up to 6 carbon atoms, or represents alkenyl which has up to 4 carbon atoms and is optionally substituted by halogen, optionally halogen-substituted phenyl or $C_{1-4}$-alkoxycarbonyl, or represents an oxime radical of the general formula

wherein

R⁴ and R⁵ have the meanings indicated above for this formula, but preferably represent cyano or phenyl, or R¹¹ represents dioxanyl, which is substituted by a radical identical to that to which R¹¹ is bonded, or R¹¹ represents a radical identical to that to which it is bonded, or R¹¹ represents phenyl which is optionally substituted by methyl, nitro, cyano, halogen or methylthio, or R¹¹ (preferably) represents a hetero-aromatic ring, such as pyridine, quinoline, quinoxaline, pyrimidine, diazinone or benzo-1,2,4-triazine, optionally substituted by $C_{1-4}$-alkyl and/or by halogen, are particularly preferred.

Specific compounds (C) which may be mentioned are: O,O-dimethyl or O,O-diethyl O-(2,2-dichloro- or 2,2-dibromovinyl) phosphoric acid ester, O,O-diethyl O-(4-nitro-phenyl) thionophosphoric acid ester, O,O-dimethyl O-(3-methyl-4-methylthio-phenyl) thionophosphoric acid ester, O,O-dimethyl O-(3-methyl-4- nitro-phenyl) thionophosphoric acid ester, O-ethyl S-n-propyl O-(2,4-dichlorophenyl) thionophosphoric acid ester, O-ethyl S-n-propyl O-(4-methylthio-phenyl)-thionophosphoric acid ester, O,O-dimethyl S-(4-oxo-1,2,3-benzotriazin-3-yl-methyl) thionothiolphosphoric acid ester, O-methyl O-(2-iso-propyl-6-methoxy-pyrimidin-4-yl) thionomethanephosphonic acid ester, O,O-diethyl O-(2-iso-propyl-6-methylpyrimidin-4-yl) thionophosphoric acid ester, O,O-diethyl O-(3-chloro-4-methyl-coumarin-7-yl) thionophosphoric acid ester, O,O-dimethyl 2,2,2-trichloro-1-hydroxy-ethanephosphonic acid ester and O,O-dimethyl S-(methylcarbamoylmethyl) thionophosphoric acid ester.

Preferred halogenoalkanes (D) are those of the general formula

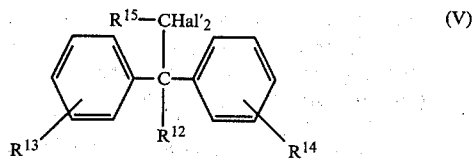

in which

Hal' represents chlorine or bromine, $R^{12}$ represents hydrogen or hydroxyl, $R^{13}$ and $R^{14}$ are identical or different and represent halogen, alkyl or alkoxy and $R^{15}$ represents hydrogen or halogen. Particularly preferred halogenoalkanes of the formula (V) are those in which $R^{12}$ and $R^{13}$ denote hydrogen or hydroxyl, $R^{14}$ represents halogen, alkyl with 1 to 4 carbon atoms or alkoxy with 1 to 4 carbon atoms and $R^{15}$ denotes halogen.

Specific compounds which may be mentioned are: 1,1,1-trichloro-2,2-bis-(4-chloro- or 4-methoxy-phenyl)-ethane, 1,1,1-trichloro-2-hydroxy-2,2-bis-(4-chloro-phenyl)-ethane and 1,1-dichloro-2,2-bis-(4-ethyl-phenyl)-ethane.

Hexachlorocyclohexane is also a particularly preferred halogenoalkane within group (D).

Surprisingly, the insecticidal and/or acaricidal action of the active compound combinations according to the invention is considerably more powerful than the action of the individual components or than the sum of the actions of the individual components. It is furthermore considerably more powerful than the action of the active compound combination of 2-iso-propoxy-phenyl N-methyl-carbamate and piperonyl butoxide, which is already known. In addition, the substituted benzazoles which can be used according to the invention display an excellent synergistic activity not only with one class of active compounds but with active compounds from the most diverse groups of chemical substances.

The formula (I) provides a definition of the synergistic agents to be used for the active compound combinations according to the invention. Preferably, in this formula R represents alkyl, cycloalkyl, alkenyl or alkynyl, in each case with up to 6 carbon atoms, trifluoromethyl, cyanomethyl, benzyl or phenyl which optionally carries one or more substituents selected from $C_{1-4}$-alkyl, halogen, $C_{1-4}$-alkoxy, nitro, cyano, $C_{1-4}$-alkylthio, $C_{1-4}$-alkylcarbonyl and $C_{1-4}$-alkoxycarbonyl, $R^1$, $R^2$, $R^3$ and $R^4$ independently of one another represent hydrogen, halogen, $C_{1-4}$-alkyl, $C_{1-4}$-alkoxy or nitro or two radicals in combination represent benzo;

X and Y independently of one another represent oxygen or sulphur and n represents zero or 1.

Examples which may be mentioned of the benzazoles of the formula (I) to be used, according to the invention, as synergistic agents are: 2-methyl-, 2-ethyl-, 2-n-propyl-, 2-iso-propyl-, 2-n-butyl-, 2-iso-butyl-, 2-sec.-butyl-, 2-tert.-butyl-, 2-n-pentyl-, 2-iso-pentyl-, 2-sec.-pentyl-, 2-tert.-pentyl-, 2-trifluoromethyl-, 2-methoxy-, 2-ethoxy-, 2-n-propoxy-, 2-iso-propoxy-, 2-n-butoxy-, 2-iso-butoxy-, 2-sec.-butoxy-, 2-tert.-butoxy-, 2-n-pentoxy-, 2-iso-pentoxy-, 2sec.-pentoxy-, 2-tert.-pentoxy-, 2-methylthio-, 2-ethylthio-, 2-n-propylthio-, 2-iso-propylthio-, 2-n-butylthio-, 2-iso-butylthio-, 2-sec.-butylthio-, 2-tert.-butylthio-, 2-n-pentylthio-, 2-iso-pentylthio-, 2-sec.-pentylthio-, 2-tert.-pentylthio-, 2-cyanomethylthio-, 2-phenylmethylthio-, 2-propen-2-oxy-, 2-propen-2-ylthio-, 2-(2-methyl-propen-2-yl)thio-, 2-propyn-2-oxy-, 2-propyn-2-ylthio-, 2-(1-methyl-propyn-2-yl)-thio-, 2-phenoxy- and 2-(3-methyl-phenoxy)-benzoxazole and -benzthiazole, as well as 2,5-dimethyl-benzoxazole and -benzthiazole, 5-methoxy- and 5-ethoxy-2-methyl-benzthiazole, 5,7-dichloro-, 5-chloro-6-nitro- and 5-chloro-7-nitro-2-methyl-benzoxazole, 5,7-dichloro-, 4,5,7-trichloro-, 4-chloro-6-nitro-, 5-chloro-6-nitro- and 5-chloro-7-nitro-2-methylthio-benzoxazole, 2-ethylthio-, 2-n-propylthio-, 2-propen-2-ylthio- and 2-propyn-2-ylthio-5,7-dichloro-benzoxazole, 2-methylthio- and 2-ethylthio-5-chloro-benzthiazole, 2-methylthio-, 2-ethylthio-, 2-n-propylthio-, 2-iso-propylthio- and 2-propen-2-ylthio-6-ethoxy-benzthiazole as well as naphtho(1,2-d)- and naphtho(2,1-d)-2-methyl-oxazole and naphtho(1,2-d)- and naphtho(2,1-d)-2-methyl-thiazole.

Those benzoazoles in which

R represents —$CH_2$—C≡—CH, $R^1$, $R^2$, $R^3$ and $R^4$ represent independently of one another hydrogen or halogen (preferably chlorine), Y represents oxygen and n represents 1, are new and exhibit particularly high synergistic activity.

Compounds of the formula (I) are known and can be prepared by processes which are known from the literature (see, for example, J. Org. Chem. 32 (1967), 2956-2959; and DE-OS (German Published Specification) No. 2,335,092).

Compounds of the formula (I) in which Y represents oxygen and n represents 1 are obtained, for example, by converting alcohols (hydroxy-alkanes, -alkenes, -alkynes, -cycloalkanes, -arylalkanes or -arenes) into the corresponding alcoholates by adding sodium or potassium at a temperature between 0° and 100° C. and then reacting these alcoholates with 2-chloro- or 2-bromo-benzoazoles- which can be substituted according to the definition of the radicals which is given under formula (I)—at a temperature between 0° and 150° C.

Working up is effected, for example, by extracting the products from the reaction mixture, which has been diluted with water, with toluene, and washing the organic phase with water, drying it and subjecting it to distillation.

Compounds of the formula (I) in which Y represents sulphur and n represents 1 are obtained, for example, by converting 2-mercapto-benzoazoles, which can be substituted according to the definition of the radicals which is given under formula (I), into the corresponding alkali metal salts with alkali metal alcoholates in alcoholic solution, for example sodium methylate in methanol, at a temperature between 0° and 100° C. and reacting these alcoholates with halogen compounds (chloro-, bromo- or iodo-alkanes, -alkenes, alkynes, -cycloalkanes, -arylalkanes or arenes) at a temperature between 0° and 150° C. Working up can be effected as described above, by extraction, washing, drying and distillation.

As already mentioned, the new active compound combinations of (1) the benzazoles of the formula (I) with (2) carbamates, carboxylic acid esters, phosphoric acid esters, phosphonic acid esters or halogenoalkanes display a considerable increase in action compared with the individual active compounds or compared with the sum thereof.

The synergistic action is especially pronounced when the benzazole component (1) and the pesticidal component (2) are present in the active compound combinations in a weight ratio of about 0.1:10 to 10:0.1, preferably about 1:3 to 3:1 and especially about 1:1.

The active compounds are well tolerated by plants, have a favorable level of toxicity to warm-blooded animals, and can be used for combating arthropod pests, especially insects and acarids, which are encountered in agriculture, in forestry, in the protection of stored products and of materials, and in the hygiene field. They are active against normally sensitive and resistant species and against all or some stages of development. The above-mentioned pests include:

from the class of the Isopoda, for example *Oniscus asellus, Armadillidium vulgare* and *Porcellio scaber;* from the class of the Diplopoda, for example *Blaniulus guttulatus;* from the class of the Chilopoda, for example *Geophilus carpophagus* and *Scutigera* spec.;

from the class of the Symphyla, for example *Scutigerella immaculata;* from the order of the Thysanura, for example *Lepisma saccharina;* from the order of the Collembola, for example *Onychiurus armatus;* from the order of the Orthoptera, for example *Blatta orientalis, Periplaneta americana, Leucophaea maderae, Blattella germanica, Acheta domesticus, Gryllotalpa*spp., *Locusta migratoria migratorioides, Melanoplus differentialis* and *Schistocerca gregaria;* from the order of the Dermaptera, for example *Forficula auricularia;* from the order of the Isoptera, for example Reticulitermes spp.;

from the order of the Anoplura, for example *Phylloxera vastatrix,* Pemphigus spp., *Pediculus humanus corporis,* Haematopinus spp. and Linognathus spp.;

from the order of the Mallophaga, for example Trichodectes spp. and Damalinea spp.;

from the order of the Thysanoptera, for example *Hercinothrips femoralis* and *Thrips tabaci;* from the order of the Heteroptera, for example Eurygaster spp., *Dysdercus intermedius, Piesma quadrata, Cimex lectularius, Rhodnius prolixus* and Triatoma spp.;

from the order of the Homoptera, for example *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae,* Myzus spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae, Pseudococcus* spp. and Psylla spp.;

from the order of the Lepidoptera, for example *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp., *Bucculatrix thurberiella, Phyllocnistis citrella,* Agrotis spp., Euxoa spp., Feltia spp., *Earias insulana,* Heliothis spp., *Laphygma exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia kuehniella, Galleria mellonella, Cacoecia podana, Capua reticulana, Choristoneura fumiferana, Clysia ambiguella, Homona magnanima* and *Tortrix viridana;* from the order of the Coleoptera, for example *Anobium punctatum, Rhizopertha dominica, Bruchidius obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis* and *Costelytra zealandica;* from the order of the Hymenoptera, for example Diprion spp., Hoplocampa spp., Lasius spp., *Monomorium pharaonis* and Vespa spp.;

from the order of the Diptera, for example Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp, Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa;* from the order of the Siphonaptera, for example *Xenopsylla cheopis* and Ceratophyllus spp.;

from the class of the Arachnida, for example *Scorpio maurus* and *Latrodectus mactans;* from the order of the Acarina, for example *Acarus siro,* Argas spp., Ornithodoros spp., *Dermanyssus gallinae, Eriophyes ribis, Phyllocoptruta oleivora,* Boophilus spp., Rhipicephalus spp., Amblyomma spp., Hyalomma spp., Ioxdes spp., Psoroptes spp., Chorioptes spp., Sarcoptes spp., Tarsonemus spp., *Bryobia praetiosa,* Panonychus spp. and Tetranychus spp..

The active compounds can be converted into the customary formulations, such as solutions, emulsions, suspensions, powders, dusting agents, foams, pastes, soluble powders, granules, aerosols, suspension-emulsion concentrates, seed-treatment powders, natural and synthetic materials impregnated with active compound, very fine capsules in polymeric substances, coating compositions for use on seed, and formulations used with burning equipment, such as fumigating cartridges, fumigating cans and fumigating coils, as well as ULV cold mist and warm mist formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agent and/or foam-forming agents. In the case of the use of water as an extender, organic solvents can, for example, also be used as auxiliary solvents.

As liquid diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.1 to 95 percent by weight of active compound, preferably from 0.5 to 90 percent by weight.

The active compounds according to the invention may be used in the form of their formulations of the types that are commercially available or in the use forms prepared from these formulations.

The active compound content of the use forms prepared from the formulations of the types that are commercially available can vary within wide ranges. The active compound concentration of the use forms can be from 0.0000001 to 100% by weight of active compound, preferably from 0,0001 to 10% by weight.

The compounds may be employed in a customary manner appropriate for the particular use forms.

When used against pests harmful to health and pests of stored products, the active compounds are distinguished by an excellent residual activity on wood and clay as well as a good stability to alkali on limed substrates.

The invention also provides a method of combating pests (in particular arthropods and especially insects or acarids) which comprises applying to the pests or to a habitat thereof, a composition according to the present invention.

The invention also provides crops protected from damage by pests by being grown in areas in which immediately prior to and/or during the time of the growing, a composition according to the present invention was applied.

It will be seen that the usual methods of providing a harvested crop may be improved by the present invention.

The preparation of the synergistic agents is shown in the following illustrative example:

EXAMPLE 1

(A) 2-Alkoxy-benzazoles 0.2 mol of sodium was dissolved in the alcohol (about 200 ml) to be used, 0.2 mol of 2-chloro-benzazole was added to the solution and the reaction mixture was stirred at a bath temperature of about 100° C. After cooling, the mixture was taken up in toluene/water, the organic phase was separated off, washed with water and dried and, after filtration, the filtrate was distilled.

(B) 2-Alkylthio-benzazoles 0.2 mol of sodium was dissolved in 200 ml of methanol, 0.2 mol of 2-mercapto-benzazole and then 0.2 mol of a halogenoalkane were added to the solution and the mixture was stirred for 2 hours, during which it was heated to the boil under reflux. After cooling, the mixture was taken up in toluene/water, the organic phase was separated off, washed with water, dried and filtered and the filtrate was distilled.

The compounds of the formula (I) listed in the following table in which n is 1 could be synthesized according to (A) or (B):

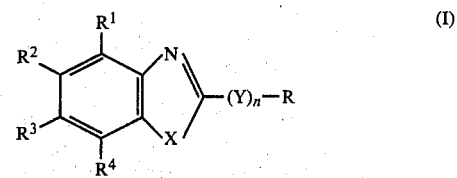

TABLE 1

| Compound No. | R¹ | R² | R³ | R⁴ | X | Y | R | Boiling point (°C./mbars) |
|---|---|---|---|---|---|---|---|---|
| 1 | H | H | H | H | S | O | CH$_3$ | 80/1.5 |
| 2 | H | H | H | H | S | O | C$_2$H$_5$ | 95/3 |
| 3 | H | H | H | H | S | O | CH(CH$_3$)$_2$ | 106/3 |
| 4 | H | H | H | H | S | O | C(CH$_3$)$_3$ | 92/3 |
| 5 | H | H | H | H | S | O | C$_3$H$_7$—n | 104/4 |
| 6 | H | H | H | H | S | O | C$_4$H$_9$—n | 119/3 |
| 7 | H | H | H | H | S | O | CH—CH$_2$—CH$_3$<br>\|<br>CH$_3$ | $n_D^{21}$ = 1.5312 |
| 8 | H | H | H | H | S | O | CH$_2$—CH(CH$_3$)$_2$ | $n_D^{21}$ = 1.5172 |
| 9 | H | H | H | H | S | O | CH$_2$CH$_2$CH(CH$_3$)$_2$ | $n_D^{21}$ = 1.5098 |
| 10 | H | H | H | H | S | O | C$_5$H$_{11}$—n | $n_D^{21}$ = 1.5102 |
| 11 | H | H | H | H | O | O | CH(CH$_3$)$_2$ | 74/2 |
| 12 | H | H | H | H | S | S | CH$_3$ | 104/3 |
| 13 | H | H | H | H | S | S | C$_2$H$_5$ | 116/3 |
| 14 | H | H | H | H | S | S | CH(CH$_3$)$_2$ | 115/1.5 |
| 15 | H | H | H | H | S | S | C$_3$H$_7$—n | 120/4 |
| 16 | H | H | H | H | S | S | CH$_2$CH(CH$_3$)$_2$ | 132/3 |
| 17 | H | H | H | H | S | S | C$_4$H$_9$—n | 130/1.5 |
| 18 | H | H | H | H | S | S | CH—CH$_2$CH$_3$<br>\|<br>CH$_3$ | 132/3 |
| 19 | H | H | H | H | S | S | CH$_2$CH$_2$CH(CH$_3$)$_2$ | 150/1.5 |
| 20 | H | H | H | H | S | S | C$_5$H$_{11}$—n | 154/1.5 |
| 21 | H | H | H | H | S | S | CH$_2$C$_6$H$_5$ | 210/4 |
| 22 | H | H | H | H | S | S | C$_6$H$_{11}$ | 172/3 |
| 23 | H | Cl | H | H | S | S | CH$_3$ | mp. 85 |
| 24 | H | Cl | H | H | S | S | C$_2$H$_5$ | mp. 154 |
| 25 | H | H | OC$_2$H$_5$ | H | S | S | CH$_3$ | mp. 46 |
| 26 | H | H | OC$_2$H$_5$ | H | S | S | C$_2$H$_5$ | mp. 54 |
| 27 | H | H | OC$_2$H$_5$ | H | S | S | CH(CH$_3$)$_2$ | $n_D^{21}$ = 1.5063 |
| 28 | H | H | OC$_2$H$_5$ | H | S | S | C$_3$H$_7$—n | $n_D^{21}$ = 1.5164 |
| 29 | H | H | H | H | S | S | C(CH$_3$)$_3$ | $n_D^{21}$ = 1.5326 |
| 30 | H | Cl | H | Cl | O | S | CH$_3$ | mp. 87 |
| 31 | Cl | Cl | H | Cl | O | S | CH$_3$ | mp. 104 |
| 32 | H | Cl | H | NO$_2$ | O | S | CH$_3$ | mp. 103 |
| 33 | H | Cl | NO$_2$ | H | O | S | CH$_3$ | mp. 98 |
| 34 | H | NO$_2$ | H | Cl | O | S | CH$_3$ | mp. 116–118 |
| 35 | H | H | H | H | O | S | CH(CH$_3$)$_2$ | 102/3 |
| 36 | H | H | H | H | O | S | CH$_3$ | $n_D^{21}$ = 1.6120 |
| 37 | H | H | H | H | O | S | C$_2$H$_5$ | 96/3 |
| 38 | H | Cl | H | Cl | O | S | C$_2$H$_5$ | mp. 70 |
| 39 | H | Cl | H | Cl | O | S | C$_3$H$_7$—n | $n_D^{21}$ = 1.5912 |
| 40 | H | H | H | H | S | O | CH$_2$—C≡CH | mp. 53 |
| 41 | H | H | H | H | O | O | CH$_2$—C≡CH | 132/10 |
| 42 | H | Cl | H | H | O | O | CH$_2$—C≡CH | mp. 72 |
| 43 | H | H | NO$_2$ | H | S | O | CH$_2$—C≡CH | $n_D^{21}$ = 1.4798 |
| 44 | Cl | H | Cl | H | O | O | CH$_2$—C≡CH | mp. 91 |

The pesticidal activity of the compounds of this invention is illustrated by the following examples:

EXAMPLE 2

LT$_{100}$ test for Diptera
Test insects: *Musca domestica* (Weymanns strain)
Number of test insects: 25
Solvent: Acetone The active compounds, synergistic agents and their mixtures were dissolved in the solvent and 2.5 ml of the solutions were pipetted into a Petri dish. On the bottom of the Petri dish there was a filter paper with a diameter of about 9.5 cm which absorbs the liquids. The Petri dish remained uncovered until the solvent had completely evaporated. 25 test insects were then placed in the Petri dish and the dish was covered with a glass lid.

The condition of the test insects was continuously observed for a period of 6 hours. The time which was necessary for 100% "knock-down" was determined. If the LT$_{100}$ was not achieved after 6 hours, then the percentage of the knocked down insects was determined.

The concentrations of the active compounds, synergistic agents and mixtures and their actions can be seen from the table which follows:

TABLE 2
LT₁₀₀ test with *Musca domestica* (Weymanns strain), resistant to phosphoric acid esters
| Active compounds or synergistic agents ( ) identification letter/No. | Concentration in % | LT₁₀₀ after minutes |
|---|---|---|
| 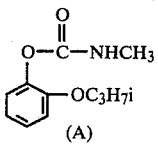 (A) | 1.0 | 360' = 0% |
| 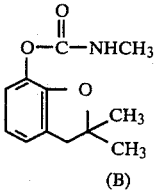 (B) | 1.0 | 360' = 20% |
| 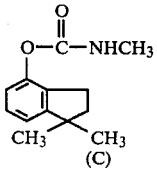 (C) | 1.0 | 360' = 0% |
| 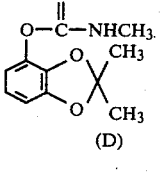 (D) | 1.0 | 360' = 0% |
| 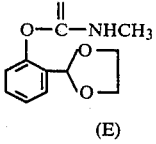 (E) | 1.0 | 360' = 0% |
| 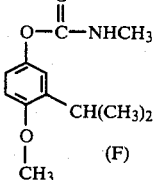 (F) | 1.0 | 360' = 0% |
| 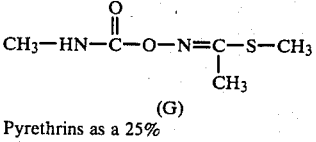 (G) | 0.2 | 360' = 65% |
| Pyrethrins as a 25% strength extract (H) | 0.04 | 360' = 60% |
| 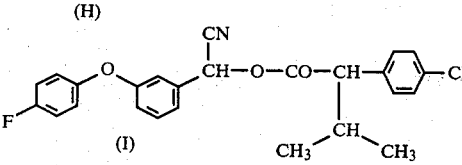 (I) | 0.04 | 240' |
| 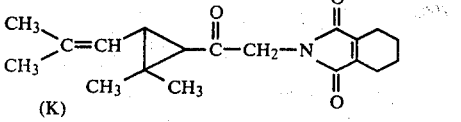 (K) | 0.04 | 360' = 45% |

TABLE 2-continued

LT$_{100}$ test with *Musca domestica* (Weymanns strain), resistant to phosphoric acid esters

| Active compounds or synergistic agents ( ) identification letter/No. | Concentration in % | LT$_{100}$ after minutes |
|---|---|---|
| (L) Cl₂C=CH—cyclopropane(CH₃)₂—C(=O)—O—CH₂—C₆H₄—O—C₆H₅ (cis, H,H) | 0.004 | 105' |
| (M) (CH₃)₂C=CH—cyclopropane(CH₃,CH₃)—C(=O)—O—CH₂—furan—CH₂—C₆H₅ | 0.04 | 210' = |
| (N) Cl₂C=CH—cyclopropane(CH₃,CH₃)—C(=O)—O—CH(CN)—C₆H₃(F)—O—C₆H₄F | 0.008 | 360' = 95% |
| (O) Cl₂C=CH—cyclopropane(CH₃,CH₃)—C(=O)—O—CH₂—C₆F₅ (−) trans | 0.0016 | 150' |
| (P) Cl,Cl-C₆H₃—CH(CCl₃)—O—C(=O)—CH₃ | 1.0 | 360' = 10% |
| (Q) C₆H(Cl)₆ (hexachlorocyclohexane) | 1.0 | 360' |
| (R) (4-Cl-C₆H₄)₂CH—CCl₃ | 1.0 | 360' = 5% |
| (S) (4-CH₃O-C₆H₄)₂CH—CCl₃ | 1.0 | 360' = 10% |
| (T) CCl₂=CH—O—P(=O)(OCH₃)₂ | 0.008 | 360' = 80% |
| (U) CH₃HN—C(=O)—CH₂—S—P(=O)(OCH₃)₂ | 0.2 | 360' = 80% |

TABLE 2-continued
LT$_{100}$ test with *Musca domestica* (Weymanns strain), resistant to phosphoric acid esters
| Active compounds or synergistic agents ( ) identification letter/No. | Concentration in % | LT$_{100}$ after minutes |
|---|---|---|
| 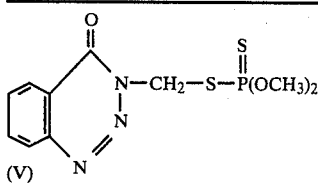 (V) | 1.0 | 360' = 0% |
| 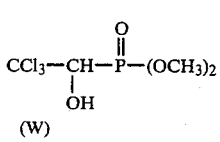 (W) | 1.0 | 360' = 0 |
| 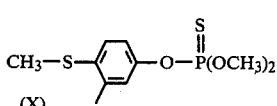 (X) | 0.2 | 360' = 10% |
| 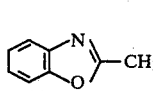 (1) | 1.0 | 360' = 0% |
| 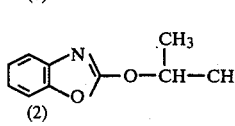 (2) | 1.0 | 360' = 0% |
| 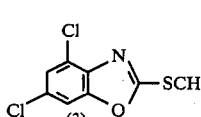 (3) | 1.0 | 360' = 0% |
| 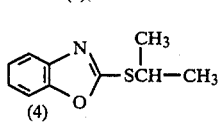 (4) | 1.0 | 360' |
| 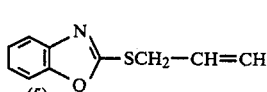 (5) | 0.2 | 360' = 80% |
| 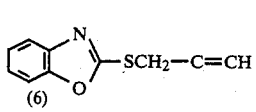 (6) | 0.2 | 360' = 50% |
| 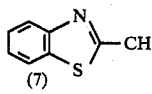 (7) | 0.2 | 360' = 35% |
| 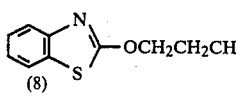 (8) | 1.0 | 360' = 90% |
| 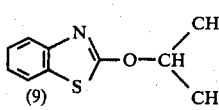 (9) | 1.0 | 360' = 80% |
| 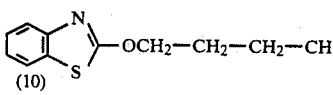 (10) | 0.2 | 360' = 35% |

TABLE 2-continued

LT$_{100}$ test with *Musca domestica* (Weymanns strain), resistant to phosphoric acid esters

| Active compounds or synergistic agents ( ) identification letter/No. | Concentration in % | LT$_{100}$ after minutes |
|---|---|---|
| (11) benzothiazole-2-O-C(CH$_3$)$_3$ | 1.0 | 360' = 0% |
| (12) benzothiazole-2-SCH$_3$ | 0.2 | 240' |
| (13) 5-Cl-benzothiazole-2-SCH$_3$ | 1.0 | 360' = 15% |
| (14) benzothiazole-2-S-CH(CH$_3$)$_2$ | 0.2 | 360' = 5% |
| (15) benzothiazole-2-SCH$_2$-CH=CH$_2$ | 1.0 | 360' = 80% |
| (16) benzothiazole-2-S-CH$_2$-C≡CH | 1.0 | 360' = 0% |
| (17) benzothiazole-2-S-CH(CH$_3$)-C≡CH | 1.0 | 360' = 60% |
| Comparison agent: Piperonyl butoxide | 1.0 | 360' = 0% |

| Identification letter of the active compound | + | Synergistic agent No. | Active compound | + | Synergistic agent | LT 100 after minutes |
|---|---|---|---|---|---|---|
| A | + | Piperonyl butoxide (Comparison agent) | 0.2 | + | 0.2 | 360' = 60% |
| A | + | 1 | 0.2 | + | 0.2 | 360' = 90% |
| A | + | 6 | 0.04 | + | 0.04 | 180' |
| A | + | 7 | 0.2 | + | 0.2 | 240' |
| A | + | 8 | 0.2 | + | 0.2 | 210' |
| A | + | 10 | 0.2 | + | 0.2 | 360' |
| A | + | 14 | 0.2 | + | 0.2 | 240' |
| B | + | Piperonyl butoxide (Comparison agent) | 1.0 | + | 1.0 | 210' |
| B | + | 1 | 0.2 | + | 0.2 | 150' |
| B | + | 2 | 1.0 | + | 1.0 | 60' |
| B | + | 4 | 0.2 | + | 0.2 | 150' |
| B | + | 6 | 0.04 | + | 0.04 | 120' |
| B | + | 7 | 0.04 | + | 0.04 | 180' |
| B | + | 8 | 0.2 | + | 0.2 | 75' |
| B | + | 9 | 0.2 | + | 0.2 | 90' |
| B | + | 10 | 0.2 | + | 0.2 | 150' |
| B | + | 11 | 0.2 | + | 0.2 | 105' |
| B | + | 12 | 0.2 | + | 0.2 | 105' |
| B | + | 14 | 0.04 | + | 0.04 | 210' |
| B | + | 15 | 0.2 | + | 0.2 | 180' |
| B | + | 16 | 0.2 | + | 0.2 | 210' |
| B | + | 17 | 0.04 | + | 0.04 | 180' |
| C | + | Piperonyl butoxide (Comparison agent) | 1.0 | + | 1.0 | 360' = 80% |
| C | + | 1 | 1.0 | + | 1.0 | 45' |
| C | + | 7 | 0.2 | + | 0.2 | 60' |
| D | + | Piperonyl butoxide (Comparison agent) | 1.0 | + | 1.0 | 360' = 20% |
| D | + | 1 | 1.0 | + | 1.0 | 360' |

-continued

| Identification letter of the active compound | + | Synergistic agent No. | Active compound | + | Synergistic agent | LT 100 after minutes |
|---|---|---|---|---|---|---|
| D | + | 2 | 1.0 | + | 1.0 | 180' |
| D | + | 4 | 1.0 | + | 1.0 | 180' |
| D | + | 5 | 0.2 | + | 0.2 | 150' |
| D | + | 6 | 0.04 | + | 0.04 | 240' |
| D | + | 7 | 1.0 | + | 1.0 | 60' |
| D | + | 8 | 1.0 | + | 1.0 | 180' |
| D | + | 9 | 1.0 | + | 1.0 | 120' |
| D | + | 11 | 1.0 | + | 1.0 | 360' |
| D | + | 12 | 1.0 | + | 1.0 | 120' |
| D | + | 14 | 0.2 | + | 0.2 | 360' |
| D | + | 15 | 1.0 | + | 1.0 | 210' |
| D | + | 17 | 1.0 | + | 1.0 | 210' |
| E | + | Piperonyl butoxide (Comparison agent) | 1.0 | + | 1.0 | 360' = 15% |
| E | + | 1 | 0.2 | + | 0.2 | 150' |
| E | + | 2 | 0.2 | + | 0.2 | 360' = 95% |
| E | + | 7 | 0.2 | + | 0.2 | 75' |
| E | + | 8 | 1.0 | + | 1.0 | 120' |
| E | + | 9 | 0.2 | + | 0.2 | 60' |
| E | + | 10 | 0.2 | + | 0.2 | 105' |
| E | + | 11 | 0.2 | + | 0.2 | 240' |
| E | + | 12 | 0.2 | + | 0.2 | 105' |
| E | + | 14 | 0.2 | + | 0.2 | 180' |
| E | + | 15 | 1.0 | + | 1.0 | 180' |
| E | + | 16 | 1.0 | + | 1.0 | 210' |
| F | + | Piperonyl butoxide (Comparison agent) | 1.0 | + | 1.0 | 360' = 90% |
| F | + | 9 | 1.0 | + | 1.0 | 180' |
| F | + | 12 | 0.2 | + | 0.2 | 180' |
| F | + | 14 | 0.2 | + | 0.2 | 180' |
| G | + | Piperonyl butoxide (Comparison agent) | 0.2 | + | 0.2 | 360' = 95% |
| G | + | 2 | 0.2 | + | 0.2 | 90' |
| G | + | 4 | 0.2 | + | 0.2 | 90' |
| G | + | 5 | 0.2 | + | 0.2 | 120' |
| G | + | 6 | 0.2 | + | 0.2 | 60' |
| G | + | 8 | 0.2 | + | 0.2 | 75' |
| G | + | 9 | 0.2 | + | 0.2 | 75' |
| G | + | 10 | 0.2 | + | 0.2 | 120' |
| G | + | 11 | 0.2 | + | 0.2 | 150' |
| G | + | 12 | 0.2 | + | 0.2 | 105' |
| G | + | 14 | 0.2 | + | 0.2 | 75' |
| G | + | 15 | 0.2 | + | 0.2 | 105' |
| G | + | 16 | 0.2 | + | 0.2 | 120' |
| G | + | 17 | 0.2 | + | 0.2 | 150' |
| H | + | Piperonyl butoxide (Comparison agent) | 0.04 | + | 0.04 | 150' |
| H | + | 2 | 0.04 | + | 0.04 | 120' |
| H | + | 4 | 0.04 | + | 0.04 | 105' |
| H | + | 5 | 0.04 | + | 0.04 | 75' |
| H | + | 6 | 0.04 | + | 0.04 | 60' |
| H | + | 10 | 0.04 | + | 0.04 | 90' |
| H | + | 12 | 0.04 | + | 0.04 | 75' |
| H | + | 13 | 0.04 | + | 0.04 | 120' |
| H | + | 15 | 0.04 | + | 0.04 | 60' |
| H | + | 16 | 0.04 | + | 0.04 | 120' |
| H | + | 17 | 0.04 | + | 0.04 | 90' |
| I | + | Piperonyl butoxide (Comparison agent) | 0.04 | + | 0.04 | 150' |
| I | + | 4 | 0.04 | + | 0.04 | 90' |
| I | + | 5 | 0.04 | + | 0.04 | 75' |
| I | + | 6 | 0.04 | + | 0.04 | 75' |
| I | + | 7 | 0.04 | + | 0.04 | 75' |
| I | + | 8 | 0.04 | + | 0.04 | 75' |
| I | + | 9 | 0.04 | + | 0.04 | 105' |
| I | + | 10 | 0.04 | + | 0.04 | 60' |
| I | + | 12 | 0.04 | + | 0.04 | 90' |
| I | + | 13 | 0.04 | + | 0.04 | 105' |
| I | + | 14 | 0.04 | + | 0.04 | 90' |
| I | + | 15 | 0.04 | + | 0.04 | 90' |
| I | + | 16 | 0.04 | + | 0.04 | 90' |
| I | + | 17 | 0.04 | + | 0.04 | 75' |
| K | + | Piperonyl butoxide | 0.04 | + | 0.04 | $6^h$ |
| K | + | 2 | 0.04 | + | 0.04 | 150' |
| K | + | 3 | 0.04 | + | 0.04 | 120' |
| K | + | 4 | 0.04 | + | 0.04 | 75' |
| K | + | 5 | 0.04 | + | 0.04 | 90' |
| K | + | 6 | 0.04 | + | 0.04 | 60' |
| K | + | 8 | 0.04 | + | 0.04 | 120' |

-continued

| Identification letter of the active compound | + | Synergistic agent No. | Concentrations in % Active compound | + | Synergistic agent | LT 100 after minutes |
|---|---|---|---|---|---|---|
| K | + | 10 | 0.04 | + | 0.04 | 60' |
| K | + | 12 | 0.04 | + | 0.04 | 60' |
| K | + | 13 | 0.04 | + | 0.04 | 105' |
| K | + | 14 | 0.04 | + | 0.04 | 75' |
| K | + | 15 | 0.04 | + | 0.04 | 60' |
| K | + | 16 | 0.04 | + | 0.04 | 60' |
| K | + | 17 | 0.04 | + | 0.04 | 105' |
| L | + | Piperonyl butoxide | 0.04 | + | 0.04 | 210' |
| L | + | 4 | 0.04 | + | 0.04 | 45' |
| L | + | 5 | 0.04 | + | 0.04 | 60' |
| L | + | 6 | 0.04 | + | 0.04 | 45' |
| L | + | 8 | 0.04 | + | 0.04 | 75' |
| L | + | 10 | 0.04 | + | 0.04 | 45' |
| L | + | 11 | 0.04 | + | 0.04 | 60' |
| L | + | 13 | 0.04 | + | 0.04 | 45' |
| L | + | 15 | 0.04 | + | 0.04 | 45' |
| L | + | 16 | 0.04 | + | 0.04 | 45' |
| L | + | 17 | 0.04 | + | 0.04 | 75' |
| M | + | Piperonyl butoxide | 0.04 | + | 0.04 | 90' |
| M | + | 1 | 0.04 | + | 0.04 | 60' |
| M | + | 3 | 0.04 | + | 0.04 | 60' |
| M | + | 4 | 0.04 | + | 0.04 | 45' |
| M | + | 6 | 0.04 | + | 0.04 | 45' |
| M | + | 7 | 0.04 | + | 0.04 | 60' |
| M | + | 8 | 0.04 | + | 0.04 | 45' |
| M | + | 9 | 0.04 | + | 0.04 | 60' |
| M | + | 10 | 0.04 | + | 0.04 | 45' |
| M | + | 11 | 0.04 | + | 0.04 | 60' |
| M | + | 12 | 0.04 | + | 0.04 | 75' |
| M | + | 14 | 0.04 | + | 0.04 | 45' |
| M | + | 15 | 0.04 | + | 0.04 | 30' |
| M | + | 16 | 0.04 | + | 0.04 | 30' |
| M | + | 17 | 0.04 | + | 0.04 | 45' |
| N | + | Piperonyl butoxide | 0.008 | + | 0.008 | 120' |
| N | + | 2 | 0.008 | + | 0.008 | 90' |
| N | + | 4 | 0.008 | + | 0.008 | 105' |
| N | + | 6 | 0.008 | + | 0.008 | 90' |
| O | + | Piperonyl butoxide | 0.0016 | + | 0.0016 | 180' |
| O | + | 3 | 0.0016 | + | 0.0016 | 90' |
| O | + | 5 | 0.0016 | + | 0.0016 | 60' |
| O | + | 6 | 0.0016 | + | 0.0016 | 90' |
| O | + | 8 | 0.0016 | + | 0.0016 | 105' |
| O | + | 10 | 0.0016 | + | 0.0016 | 120' |
| O | + | 13 | 0.0016 | + | 0.0016 | 60' |
| O | + | 15 | 0.0016 | + | 0.0016 | 120' |
| P | + | Piperonyl butoxide | 1.0 | + | 1.0 | 360' = 50% |
| P | + | 1 | 1.0 | + | 1.0 | 45' |
| P | + | 7 | 0.2 | + | 0.2 | 360' = 95% |
| P | + | 9 | 0.2 | + | 0.2 | 360' = 95% |
| P | + | 10 | 0.2 | + | 0.2 | 360' |
| P | + | 11 | 0.2 | + | 0.2 | 360' |
| P | + | 12 | 0.04 | + | 0.04 | 360' |
| P | + | 14 | 0.2 | + | 0.2 | 360' = 95% |
| Q | + | Piperonyl butoxide | 1.0 | + | 1.0 | $6^h$ |
| Q | + | 1 | 1.0 | + | 1.0 | 75' |
| Q | + | 4 | 0.2 | + | 0.2 | 90' |
| Q | + | 7 | 0.2 | + | 0.2 | 210' |
| Q | + | 8 | 0.2 | + | 0.2 | 150' |
| Q | + | 9 | 0.04 | + | 0.04 | 210' |
| Q | + | 10 | 0.2 | + | 0.2 | 120' |
| Q | + | 11 | 0.2 | + | 0.2 | 180' |
| Q | + | 13 | 0.2 | + | 0.2 | 150' |
| Q | + | 14 | 0.04 | + | 0.04 | 210' |
| R | + | Piperonyl butoxide | 1.0 | + | 1.0 | 360' = 20% |
| R | + | 1 | 1.0 | + | 1.0 | 360' = 85% |
| R | + | 7 | 1.0 | + | 1.0 | 45' |
| R | + | 9 | 1.0 | + | 1.0 | 120' |
| R | + | 10 | 1.0 | + | 1.0 | 90' |
| R | + | 12 | 1.0 | + | 1.0 | 60' |
| R | + | 13 | 0.2 | + | 0.2 | 360' |
| R | + | 14 | 0.2 | + | 0.2 | 360' |
| S | + | Piperonyl butoxide | 1.0 | + | 1.0 | 360' = 85% |
| S | + | 1 | 1.0 | + | 1.0 | 105' |
| S | + | 4 | 1.0 | + | 1.0 | 105' |
| S | + | 5 | 1.0 | + | 1.0 | 75' |
| S | + | 6 | 1.0 | + | 1.0 | 105' |
| S | + | 7 | 1.0 | + | 1.0 | 30' |
| S | + | 8 | 1.0 | + | 1.0 | 180' |
| S | + | 9 | 0.2 | + | 0.2 | 150' |

-continued

| Identification letter of the active compound | + | Synergistic agent No. | Concentrations in % | | | LT 100 after minutes |
|---|---|---|---|---|---|---|
| | | | Active compound | + | Synergistic agent | |
| S | + | 10 | 1.0 | + | 1.0 | 60' |
| S | + | 11 | 1.0 | + | 1.0 | 90' |
| S | + | 12 | 0.2 | + | 0.2 | 105' |
| S | + | 14 | 1.0 | + | 1.0 | 105' |
| S | + | 17 | 1.0 | + | 1.0 | 180' |
| T | + | Piperonyl butoxide | 0.008 | + | 0.008 | 360' |
| T | + | 10 | 0.008 | + | 0.008 | 240' |
| T | + | 11 | 0.008 | + | 0.008 | 120' |
| U | + | Piperonyl butoxide | 0.2 | + | 0.2 | 210' |
| U | + | 4 | 0.2 | + | 0.2 | 90' |
| U | + | 6 | 0.2 | + | 0.2 | 75' |
| U | + | 8 | 0.2 | + | 0.2 | 75' |
| U | + | 9 | 0.2 | + | 0.2 | 60' |
| U | + | 10 | 0.2 | + | 0.2 | 60' |
| U | + | 12 | 0.2 | + | 0.2 | 60' |
| U | + | 14 | 0.2 | + | 0.2 | 60' |
| U | + | 15 | 0.2 | + | 0.2 | 120' |
| U | + | 16 | 0.2 | + | 0.2 | 120' |
| U | + | 17 | 0.2 | + | 0.2 | 105' |
| V | + | Piperonyl butoxide | 1.0 | + | 1.0 | 360' |
| V | + | 4 | 1.0 | + | 1.0 | 75' |
| V | + | 5 | 1.0 | + | 1.0 | 75' |
| V | + | 8 | 1.0 | + | 1.0 | 120' |
| V | + | 9 | 1.0 | + | 1.0 | 75' |
| V | + | 11 | 1.0 | + | 1.0 | 105' |
| V | + | 12 | 1.0 | + | 1.0 | 75' |
| V | + | 14 | 1.0 | + | 1.0 | 60' |
| W | + | Piperonyl butoxide | 1.0 | + | 1.0 | 360' = 90% |
| W | + | 6 | 1.0 | + | 1.0 | 150' |
| W | + | 7 | 1.0 | + | 1.0 | 150' |
| W | + | 9 | 0.2 | + | 0.2 | 120' |
| W | + | 11 | 1.0 | + | 1.0 | 90' |
| W | + | 14 | 0.2 | + | 0.2 | 150' |
| X | + | Piperonyl butoxide | 0.2 | + | 0.2 | 360' = 20% |
| X | + | 1 | 0.2 | + | 0.2 | 150' |
| X | + | 7 | 0.2 | + | 0.2 | 360' |
| X | + | 8 | 0.2 | + | 0.2 | 210' |
| X | + | 9 | 0.2 | + | 0.2 | 360' |
| X | + | 10 | 0.2 | + | 0.2 | 180' |
| X | + | 11 | 0.2 | + | 0.2 | 360' |
| X | + | 14 | 0.2 | + | 0.2 | 240' |
| X | + | 15 | 0.2 | + | 0.2 | 240' |
| X | + | 17 | 0.2 | + | 0.2 | 360' |

It will be appreciated that the instant specification and examples are set forth by way of illustration and not limitation, and that various modifications and changes may be made without departing form the spirit and scope of the present invention.

What we claim is:

1. A synergistic insecticidally or acaricidally active composition comprising (a) at least one insecticidally or acaricidally active compound, and (b) an amount, sufficient to render the composition pesticidally active, of a 2-substituted benzazole of the formula

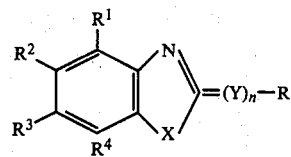

in which
R represents optionally substituted alkyl, alkenyl or alkynyl,
$R^1$, $R^2$, $R^3$ and $R^4$ independently of one another represent hydrogen or halogen,
X and Y independently of one another represent oxygen or sulphur and
n represents zero or 1.

2. A composition according to claim 1, in which R represents alkyl, alkenyl or alkynyl, in each case with up to 6 carbon atoms.

3. A composition according to claim 1, in which
R represents —$CH_2$—C≡CH,
Y represents oxygen and
n represents 1.

4. A composition according to claim 1, in which (a) is selected from the group consisting of (A) carbamates, (B) carboxylic acid esters, including natural and synthetic pyrethroids, (C) phosphoric acid esters and phosphonic acid esters and (D) halogenoalkanes.

5. A composition according to claim 1, in which
(a) is selected from the group consisting of (A) carbamates of the formula

in which
$R^1$ represents aryl, a heterocyclic radical or an oxime radical, each being optionally substituted,
$R^2$ represents hydrogen or an alkyl radical with 1 to 4 carbon atoms and $R^3$ represents alkyl, alkylcarbonyl with 1 to 6 carbon atoms in the alkyl radical, which can optionally also be substituted by hydroxyl or methylthio, or the radical —S—Z, wherein Z represents an aliphatic radical which has 1 to 4 carbon atoms and is optionally substituted by halogen, or represents an aryl radical which is optionally substituted by nitrile, halogen, methyl, trihalogenomethyl, trifluoromethylmercapto or nitro, or represents methoxycarbonyl or the radical

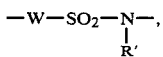

wherein R' represents hydrogen or methyl and W represents alkyl, halogenoalkyl, alkylamino, dialkylamino or an aryl radical which is optionally substituted by halogen, trihalogenomethyl, nitrile, methyl or nitro;

(B) carboxylic acid esters of the formula

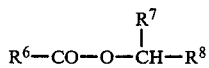

in which $R^6$ represents an alkyl, aralkyl, aryl or cycloalkyl radical which can optionally be substituted, $R^7$ represents hydrogen, alkyl, halogenoalkyl, alkenyl, alkynyl or cyano and $R^8$ represents aryl or a heterocyclic radical, or $R^7$ and $R^8$, together with the methine group to which they are bonded, form an optionally substituted cyclopentenone ring;

(C) phosphoric acid esters and phosphonic acid esters of the formula

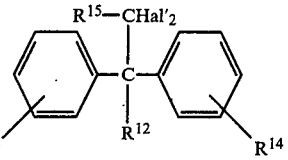

in which the radicals X' independently of one another represent O or S,

Y' represents O, S, —NH— or a direct bond between the central P atom and $R^{11}$, $R^9$ and $R^{10}$ are identical or different and represent an optionally substituted alkyl or aryl radical and $R^{11}$ represents an optionally substituted alkyl, aryl, heteroaryl, aralkyl, alkenyl or dioxanyl radical, an oxime radical or a radical identical to that to which it is bonded; and (D) halogenoalkanes of the formula $$R^{15}-CHal'_2 \diagdown \diagup \diagdown \diagup$$

(structure with two phenyl rings bearing $R^{13}$ and $R^{14}$, central C with $R^{12}$)

in which

Hal' represents chlorine or bromine, $R^{12}$ represents hydrogen or hydroxyl, $R^{13}$ and $R^{14}$ are identical or different and represent halogen, alkyl or alkoxy and $R^{15}$ represents hydrogen or halogen, and hexachlorocyclohexane.

6. A composition according to claim 1, wherein the components (a) and (b) are present in a weight ratio of about 0.1:10 to 10:1.

7. A method of combating pests which comprises applying to such pests or to a habitat thereof a pesticidally effective amount of a composition according to claim 1.

* * * * *